(12) United States Patent
Schiraldi et al.

(10) Patent No.: US 6,433,236 B1
(45) Date of Patent: Aug. 13, 2002

(54) ACID CATALYZED ISOMERIZATION OF SUBSTITUTED DIARYLS

(75) Inventors: David Anthony Schiraldi, Charlotte, NC (US); Alexei Viktorovich Iretski, Atlanta, GA (US); Sheldon Christopher Sherman, Snellville, GA (US); Laren Malcolm Tolbert, Marietta, GA (US); Mark Gilmore White, Woodstock, GA (US)

(73) Assignee: Arteva North America S.A.R.L., Zurich (CH)

( * ) Notice: Subject to any disclaimer, the term of this patent is extended or adjusted under 35 U.S.C. 154(b) by 0 days.

(21) Appl. No.: 09/531,248

(22) Filed: Mar. 21, 2000

(51) Int. Cl.$^7$ ................................................. C07C 5/22
(52) U.S. Cl. .......................... 585/477; 585/25; 585/27; 568/722; 568/723; 568/729; 568/730; 568/783
(58) Field of Search ............................ 585/477, 25, 27; 568/722, 723, 729, 730, 783

(56) References Cited

U.S. PATENT DOCUMENTS

| | | | | |
|---|---|---|---|---|
| 4,822,923 A | * | 4/1989 | Li | 568/724 |
| 5,001,281 A | * | 3/1991 | Li | 568/727 |
| 5,015,784 A | * | 5/1991 | Rudolph et al. | 568/722 |
| 5,105,026 A | * | 4/1992 | Powell et al. | 568/727 |

FOREIGN PATENT DOCUMENTS

| JP | 76038710 | 10/1976 |
|---|---|---|
| JP | 08099914 | 4/1996 |

OTHER PUBLICATIONS

Iataaki et al., *J.Org.Chem.* vol. 38, No. 1, 76–79 (1973).
Yashimoto et al., *Bull. Chem. Soc. Jpn.* 46, 2490–92 (1973).
Shiotani, *J Molecular Catalysis,* 34 (1986) 57–66.
Shiotani, *J Molecular Catalysis,* 18 (1983) 23–31.
Mende, et al., *Tet. Letters* No. 43, (1970) 3747–3750.

* cited by examiner

*Primary Examiner*—Walter D. Griffin
(74) *Attorney, Agent, or Firm*—Gregory N. Clements

(57) ABSTRACT

A substituted diaryl compound or a mixture of substituted diaryl compounds, such as dimethylbiaryl compounds are isomerized by treatment with a strong acid or mixtures of strong acids in the absence of any additional catalyst. The strong acid or mixture of acids has a Hammett acidity of less than about –12.6. The isomerization reaction conditions such as reaction temperature, amount of acid, and amount of solvent can be adjusted to selectively produce desired isomers in high yields. One or more desired isomers may be produced in high yields by isomerization of substituted diaryl compounds and selectively removing one or more desired isomers from the resulting equilibrium mixture of isomers. The isomer mixture may be re-isomerized subsequent to selective removal of the desired isomer to produce additional amounts of desired isomer. The isomerization may be employed to substantially reduce the amount of at least one isomer substituted in the 2-position or to substantially increase the amount of at least one isomer substituted in at least the 3-position, the 4-position or the 4-position for the production of at least substantially linear or crystalline polymers.

49 Claims, No Drawings

ACID CATALYZED ISOMERIZATION OF SUBSTITUTED DIARYLS

FIELD OF THE INVENTION

The invention relates to a method of isomerization of substituted diaryl compounds by treating the diaryl compounds with a strong acid. The invention is further related to a method of isomerizing a mixture of isomers, selectively removing one or more desired isomers and re-isomerizing the remaining isomers.

BACKGROUND OF THE INVENTION

Substituted diaryl compounds, such as dimethylbiphenyls, and other various substituted diphenyl derivatives can be easily functionalized to produce other compounds such as bibenzoic acid, or converted to monomers for production of various high performance polymers such as polyesters or polyamides. While all of the isomers of substituted diaryl compounds can be functionalized, certain isomers are preferred due to their geometry that gives them certain structural advantages over the other isomers. For example, the 3,4'- and 4,4'-isomers of disubstituted biphenyl are strongly preferred to the other four isomers due to their linearity. Linearity and symmetry are very important when diaryl compounds are used as monomers for high performance polymers because it is the geometric structure of monomer repeat units that defines several physical properties of the resulting polymers, such as melting point, crystallinity, glass transition point and modulus. Therefore, there is a need for development of methods for selective production of certain desired monomers of substituted diaryl compounds in high yields while minimizing yields of other isomers.

Substituted diaryl compounds can be obtained directly from petroleum refining operations, or functionalization of refinery products, but more commonly are produced by coupling of substituted monoaryl compounds.

Coupling various substituted monoaryl compounds in the presence of catalytic amounts of palladium (II) acetate or aluminum chloride to obtain mixtures of biaryl isomers is reported by Iataaki et al in *J. Org. Chem.* Vol., 76–79 (1973). The reference also discloses selective separation of a single isomer from a mixture of isomers. H. Yashimoto et al, *Bull. Chem. Soc. Japan*, 46, 2490–92 also reported oxidative coupling of substituted monoaromatic compounds in the presence of catalytic amounts of palladium salts. The reaction yields a mixture of isomers, and is conducted in 2,4-pentanedione.

Oxidative dimerization of disubstituted monoaromatic compounds such as dimethylphthalate is reported by A. Shiotani in *J. Mol. Catal.* 18, 23 (1983) and *J. Mol. Catal.* 34, 57 (1986). The references disclose a catalytic reaction, requiring palladium-based catalyst, that yields mixture of isomers of tetramethylcarboxylates. No further isomerization of the mixtures is reported.

Co-pending U.S. application Ser. No. 09/111,487 to White, et al. discloses a process of coupling various monoaromatic compounds in the presence of catalytic amounts of palladium (II) compounds and a strong acid. The coupling process produces mixtures of isomers and can be adjusted to selectively produce higher amounts of desired single isomers. The process requires the presence of a palladium catalyst. No steps of isomerization subsequent to the coupling reaction, separation of a single compound or subsequent re-equilibration of the mixture of isomers are disclosed in the application.

Substituted biaryl compounds obtained by any of the above-mentioned coupling methods, from petroleum refining operations, or from functionalization of refinery products, may contain mixtures of isomers comprising some, but usually a small amount of the desired isomers with a linear or nearly linear structure.

To increase the amount of the desired isomers, several methods of isomerization of isomeric mixtures of substituted biaryl compounds have been proposed. Isomerization of dimethylbiphenyl in the presence of silica, alumina or silica-alumina catalysts is disclosed in Japanese Patent publication JP 76038710. Dimethylbiphenyl mixtures having a low content of 4,4'-dimethylbiphenyl isomer are contacted with the catalyst in the liquid phase to increase the content of the 4.4'-dimethylbiphenyl isomer. The resulting product comprises a mixture of all six isomers with about 7% of 4,4'-product.

Isomerization of single isomers of dimethylbiphenyl by photo-irradiation of the isomers is reported by Mende et al in *Tetrahedron Lett.* (43), 3747–50 (1970). The isomerization of 2,X'-isomers is possible by irradiation of the isomers at 254 nm. However, 3,X'-, and 4,4'-isomers are photostable and do not undergo photoinitiated isomerization. Isomerization of 2,X'-isomers results in a mixture of several isomers but does not produce the linear 4,4'-isomer in any measurable quantity.

Isomerization of dimethylbiphenyl is reported in Japanese Patent publication JP 08099914, published Apr. 16, 1996. In this reference, a mixture of dimethylbiphenyl isomers is isomerized in the presence of ZSM-5 and/or ZSM-11 catalysts in the vapor phase to produce a mixture with higher amounts of 3,3'-, 3,4'- and 4,4'-products.

The present invention provides a method for isomerization of a single isomer of substituted diaryl compounds or a mixture of isomers of substituted diaryl compounds to produce an equilibrium isomeric mixture with a high content of desired isomers by treating the isomer or the mixture of isomers with a strong acid. The isomerization reaction is acid catalyzed and does not require any additional catalysts. The isomerization reaction conditions can be adjusted to produce an equilibrium mixture comprising different isomers in different amounts. One or more desired isomers can be selectively removed from the equilibrium mixture and the mixture can be re-isomerized or re-equilibrated subsequent to the removal of the desired isomers. The isomerization process may be used to: 1) substantially reduce the amount or yield of at least one isomer substituted in the 2-position, or 2) substantially increase the amount of at least one isomer substituted in at least the 3-position, the 4-position or the 4'-position to obtain monomers or reactants for the production of at least substantially linear or crystalline polymers.

SUMMARY OF THE INVENTION

Isomerization of one or more substituted diaryl compounds, such as disubstituted biaryl compounds to produce high yields of substantially linear isomers, such as 4,4'- and 3,4'-substituted isomers, is achieved by treating the substituted diaryl compounds with a strong acid. The isomerization process may also be used to substantially reduce or eliminate the amount of less linear isomers such as 2-substituted isomers. Acids useful for the isomerization have a Hammett Acidity less than −12.6, preferably less than −14. Hammett Acidity, $H_0$, is defined as $Ho_0=pK_{BH+}-\log(C_{BH+}/C_B)$; where $K_{BH+}$ is the ionization constant for the indicator, $C_{BH+}$ is the concentration of the protonated indicator and $C_B$ is the concentration of unprotonated indicator. (see, *Van Nostrand's Scientific Encyclopedia*, 5th Ed.)

Diaryl compounds that may be isomerized according to the process of the present invention include one or more electron donating groups as substituents on each of the aromatic rings. Exemplary substituted diaryl compounds which may be isomerized to linear or substantially linear diaryl compounds are represented by the general formula (A):

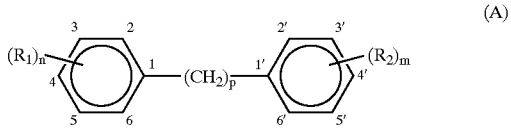

(A)

wherein both n and m are integers from 1 to 4 and may be the same or different, p is an integer from 0 to 10, each $R_1$ can be the same or different and each $R_2$ can be the same or different. Each $R_1$ and each $R_2$ is selected from groups donating electron density to the ring, or electron donating groups, such as an alkyl, aryl, amino, alkoxy, or a hydroxy group. $R_1$ and $R_2$ may be the same or different. Preferably, at least one of the substituents is selected from a hydrocarbon electron donating group, such as alkyl or aryl groups. The optional bridging group may be a branched or straight chain alkylene group. Diaryl compounds where p=0 are often referred to as biaryls or biaryl compounds.

In preferred embodiments of the invention, single isomers or mixtures of isomers of substituted biaryl compounds such as disubstituted biphenyls represented by the formula (I):

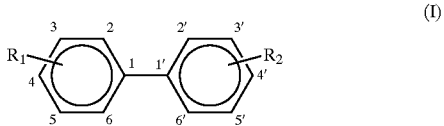

(I)

wherein $R_1$ and $R_2$ may be the same or different and are selected from various electron donating substituents, may be converted to an equilibrium isomeric mixture having a high amount of the desired 3,4' and 4,4' isomers represented by of the formulae (II) and (III), by isomerizing a single isomer or mixtures of isomers in the presence of at least one strong acid with a Hammett acidity of less than −12.6:

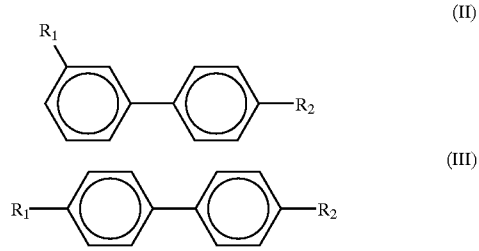

(II)

(III)

wherein $R_1$ and $R_2$ correspond to the respective $R_1$ and $R_2$ groups in the starting compounds represented by the formula (I).

The processes according to the present invention may be advantageously conducted at low temperatures and pressures in short periods of time, for example at room temperature for about 2 hours to about 20 hours, or preferably at about 100° C. for about 10 minutes to about 15 minutes, depending upon the acid to diaryl ratio used. In embodiments of the present invention reaction temperatures and times may range from about 20° C. to about 150° C. for from about 0.1 hours to about 100 hours. Reaction pressures may range from atmospheric pressure or about 14 psia to about 2000 psia.

The process according to the present invention may be used for selective production of a single desired isomer by isomerization of a single starting isomer or a mixture of isomers to produce an equilibrium mixture of isomers, selectively removing the single desired isomer, re-isomerizing or re-equilibrating of the isomer mixture subsequent to the removal of the single monomer and removing the desired isomer again or recovering the resulting mixture of isomers.

DETAILED DESCRIPTION OF THE INVENTION

A process for isomerization of substituted diaryl compounds comprising a single isomer or mixtures of several or all isomers of substituted diaryl compounds in accordance with the present invention allows for high yield of one or more of the preferred or desired isomers. Diaryl compounds, obtained from petroleum refining, functionalization of refinery products, or by coupling of monoaryl compounds and comprising mixtures of various isomers, may be converted into equilibrium mixtures with a predominant amount of desirable isomers by treating the starting isomers or their mixtures with at least one strong acid. The desirable isomers, generally, are those with a symmetrical and nearly linear structure such as 4,4'- or 3,4'-isomers of disubstituted diaryl compounds. These desirable isomers may be further functionalized and then employed for the production of polymers, such as polyesters and polyamides. While the isomerization may be conducted in the presence of a solvent, the process according to the invention does not require the presence of any substances other than the diaryl compound and the acid. The isomerization reaction is catalyzed by the strong acid and may be completed without the need for any other co-catalysts or isomerization promoters.

In embodiments of the invention, the isomerization may be employed to substantially reduce the amount of at least one isomer substituted in the 2-position of the feedstock and/or to produce or substantially increase the amount of at least one isomer substituted in at least the 3-position, the 4-position or the 4'-position in the product. For example, when one or more of the reactant or starting diaryl compounds includes at least one isomer which is substituted in at least the 2-position, the isomerization may be employed to substantially reduce the amount of at least one isomer substituted in the 2-position and to substantially increase the amount of at least one isomer substituted in at least the 3-position and the 4'-position.

In other embodiments, the isomerization may be employed to produce or substantially increase the amount of at least one isomer substituted in: 1) at least the 3-position, 2) at least the 4-position, or 3) at least the 3-position and the 4'-position, or 4) at least the 4-position and the 4'-position over the amounts of the desirable isomer products in the feedstock material. In embodiments of the invention, such feedstock material may or may not contain any 2-position isomers.

For example, in embodiments of the invention the amount of reduction of a given isomer may be at least about 25%, preferably at least about 50%, based upon the original amount of the isomer. The amount of increase of a given desired isomer may be at least about 5%, preferably at least about 10%, based upon the original amount of isomer.

Diaryl compounds that may be isomerized according to the process of the present invention include various single isomers of diaryl or biaryl compounds having at least one substituent on each of the aromatic rings and mixtures of any or all of the isomers. Exemplary substituted diaryl compounds or reactants which may be subjected to the isomerization of the present invention are represented by the general formula (A):

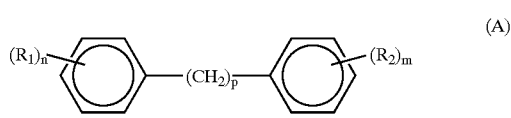

wherein both n and m are integers from 1 to 4 and may be the same or different, p is an integer from 0 to 10, and each $R_1$ and each $R_2$ can be the same or different and are selected from groups donating electron density to the ring, or electron donating groups, such as an alkyl, aryl, amino, alkoxy or a hydroxy group.

It is preferred, however, that at least one of the substituents is selected from a hydrocarbon electron donating group, such as an alkyl or an aryl group. For example, a disubstituted compound (n=m=1) with $R_1$ being a hydroxy group and $R_2$ being an alkyl group will easily undergo isomerization. However, isomerization of disubstituted compounds where none of the substituents is a hydrocarbon group may proceed at a much lower rate or to a lesser extent. Groups with election withdrawing characteristics such as carboxyl or ester groups, or halogens tend to inhibit the isomerization, and therefore the $R_1$ and $R_2$ groups generally should not be a group with electron withdrawing characteristics. If one of the groups $R_1$ or $R_2$ is an electron withdrawing group, its electron withdrawing characteristics should be balanced by another $R_1$ or $R_2$ electron donating group for the isomerization to proceed to any significant extent.

In the above formula (A) exemplary alkyl groups for $R_1$ and $R_2$ are linear or branched alkyls having one to eight carbon atoms such as methyl, ethyl, propyl, isopropyl, butyl, isobutyl, sec-butyl, tert-butyl, pentyl, isopentyl, neopentyl, hexyl, dimethylbutyl n-octyl, isooctyl, and 2-ethylhexyl.

Examples of alkoxy groups for $R_1$ and $R_2$ are those wherein at least one oxygen is bound to a linear or branched alkyl group having one to four carbon atoms. Examples of such alkoxy groups are methoxy, ethoxy, propoxy, isopropoxy, butoxy, isobutoxy, sec-butoxy, and tert-butoxy groups.

Examples of aryl groups for $R_1$ and $R_2$ are phenyl, benzyl, and alkylphenyl such as phenyl substituted with one or more lower alkyl groups.

When p is greater than 1, the alkylene group linking two aromatic rings may be a linear or branched alkylene group. Examples of alkylene groups linking the two aromatic rings are linear or branched alkylenes having one to six carbon atoms such as methylene (—$CH_2$—), ethylene (—$CH_2CH_2$—), propylene (—$CH_2CH_2CH_2$—), 2-methylpropylene (—$CH_2CH(CH_3)CH_2$—), butylene (—$CH_2CH_2CH_2CH_2$—), pentylene (—$CH_2CH_2CH_2CH_2CH_2$—), and hexylene (—$CH_2CH_2CH_2CH_2CH_2CH_2CH_2$—);

In preferred embodiments both n and m are each 1 or 2, and $R_1$ and $R_2$ are each a lower alkyl group, such as a $C_1$ to $C_4$ alkyl group, and p is less than about 5. Most preferably p is zero, and the most preferred biaryl compounds are disubstituted biphenyls.

Examples of diaryl compounds represented by the formula (A) which may be isomerized in accordance with the present invention are disubstituted diaryl compounds such as dialkylbiphenyls (p=0) (dialkyldiphenylmethanes (p=1), dialkyldiphenylethanes (p=2) and dialkyldiphenylpropanes (p=3).

Single isomers or mixtures of isomers of disubstituted biphenyls which may be isomerized in accordance with the present invention are represented by the formula (I):

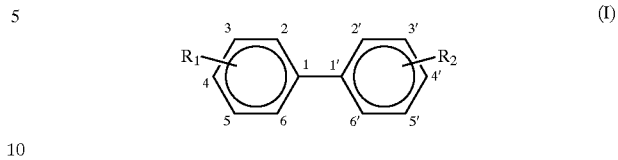

wherein $R_1$ and $R_2$ may be the same or different and are selected from various electron donating substituents as defined above for formula (A) (p=0). The disubstituted diphenyls of formula (I) may be converted to an equilibrium isomeric mixture having a high amount of the desired 3,4' and 4,4' isomers represented by the formulae (II) and (III), by isomerizing a single isomer or mixtures of isomers of formula (I) in the presence of at least one strong acid with a Hammett acidity of less than −12.6:

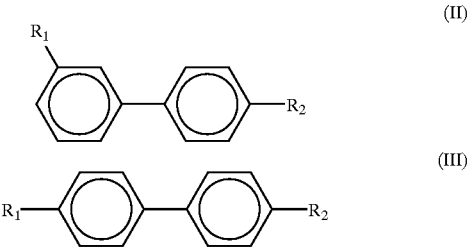

wherein $R_1$ and $R_2$ correspond to the respective $R_1$ and $R_2$ groups in the starting compounds represented by the formula (I).

Most preferably the biaryl compound of formula (I) subjected to isomerization in accordance with the present invention is any single isomer of dimethylbiphenyl or mixtures of 6 or less of dimethylbiphenyl isomers.

The strong acid employed in the present invention may be any strong acid with a Hammett acidity of lower than about −12.6. Mixtures of acids that have a Hammett acidity of less than about −12.6 may also be used in the present invention.

Examples of acids with a Hammett acidity lower than −12.6 and which may be employed as the catalytic system of the present invention are trifluoromethanesulfonic acid (hereafter referred to as triflic acid or HOTf), fluorosulfonic acid, 1:1 to 1:0.15 mixtures of antimony pentafluoride and hydrofluoric acid, and 1:0.2 mixtures of fluorosulfonic acid with either antimony pentafluoride or tantalum pentafluoride. Triflic acid has a Hammett acidity of less than −14 and is the preferred acid for use in the present invention. Various mixtures of acids, including aqueous mixtures, may also be used in the present invention as long as the Hammett acidity of the mixture is less than −12.6. For example, a mixture of triflic acid with trifluoroacetic acid can be used according to the present invention. The amount of triflic acid in a mixture with trifluoroacetic acid can be as high as 99% by weight and must be at least about 5% by weight in order for the mixture to have a Hammett acidity of less than about −12.6.

The amount of strong acid or mixture of acids added to or used in the isomerization process may be from about 0.005 moles to about 250 moles per mole of substituted diaryl compound or compounds of formula (A) subjected to the isomerization reaction. The amount of acid or the mixture of acids may depend upon the diaryl compound that is isomerized using the process according to the present invention and the amount and nature of any optional solvent employed in the isomerization reaction. The amount of the acid may also depend on the isomerization reaction temperature, and the desired isomer composition of the final product. Also a large excess of strong acid may present a problem of handling the acid, and tends to make the process less practical.

Preferred amounts of the strong acid or the mixture of acids may range from about 1 mole to about 200 moles, most preferably from about 3 moles to about 100 moles per mole of the substituted diaryl compound or substrate compound, based upon the total moles of substituted diaryl compounds or reactants. By varying the amount of the acid per mole of the substrate along with the other reaction conditions, the final product of the isomerization of reactants comprising at least one 2,X'-isomer may be substantially, essentially, or completely free of 2,X'-isomers (i.e. 2,2'-, 2,3'-, or 2,4'-isomers). Thus, at least substantially all of the 2,X'-isomers present in the reactant may be converted to other, more linear isomers and the final isomerization product may contain only the more linear 3,3'-, 3,4'- and 4,4'-isomers.

The isomerization reaction may be conducted in the presence of a solvent or without a solvent. The use of a solvent may be beneficial to dissolve solid biaryl starting material prior to the introduction of the acid for better dispersion of the starting materials in the acid. The solvent used to dissolve the substrate should be a good solvent for the starting biaromatic compounds and should not strongly interact with the acid used in the isomerization reaction. If the solvent interacts or reacts with the acid, the amount of acid used in the isomerization should be in excess to assure that a sufficient amount of unreacted acid remains in the mixture for the isomerization reaction.

Examples of solvents which may be employed are unsubstituted or monosubstituted alkyl aromatic compounds such as toluene, benzene, or aromatic compounds substituted with one or more $C_{2-C6}$ alkyl groups. Other solvents which may be used include halogenated aromatic compounds of the formula $C_6X_6$, wherein X is a halogen, such as perfluorobenzene; and paraffinic $C_nH_{2n+2}$ solvents, where n is an integer from 8 to about 30, such as n-octane. Strong acids such as trifluoroacetic acid may also be used as solvents. Polar compounds such as water or esters, and polysubstituted alkyl aromatic compounds should generally be avoided as either being a poor solvent or inhibiting the isomerization reaction. Basic solvents, including amines and amides, such as pyridine and/or dimethyl formamide, should also be avoided, as they will exothermically complex with the strong acid catalyst.

The molar ratio of the strong acid or mixture of strong acids used in the reaction to the optional solvent may be from about 0.1:1 to about 15:1, preferably from about 0.8:1 to about 10:1. The amount of solvent employed may depend upon the reactivity of the solvent towards the strong acid and the ability of the solvent to dissolve the diaryl compound. Generally the amount of solvent may be chosen to give a weight ratio of diaryl compound or substrate to the solvent from about 0.01:1 to about 1:1, preferably from about 0.1:1 to about 0.5:1.

The reaction can be run at various temperatures depending on the desired isomer composition of the final product. The reaction can be run at as low as about −10° C. or as high as 300° C., for example in the range from about 20° C. to about 150° C. Very low temperatures, such as −10° C., however, are not practical for industrial application since the reaction rate is slow and it requires a long time to complete the isomerization reaction. At temperatures in excess of 150° C. a disproportionation reaction shifting aromatic methyl groups (if present in the feedstock) from one compound to another tends to occur producing a high amount of side products comprising a mixture of higher and lower substituted diaryl compounds.

The reaction time for the isomerization may range from about 0.01 hours to about 200 hours, for example from about 2 minutes to about 100 hours, preferably from about 0.1 hour to about 2 hours. The reaction time depends on the reaction temperature, acid to substrate compound ratio, and the desired distribution of the isomers in the final product. For example, isomerization reaction times may range from about 0.1 hours to about 100 hours at reaction temperatures of from about 20° C. to about 150° C. In embodiments of the invention, the isomerization reaction may be conducted at room temperature for about 2 hours to about 20 hours, preferably from about 3 hours to about 5 hours, depending, for example, upon the amount of acid employed. In preferred embodiments, a reaction time of about 10 minutes to about 15 minutes at a reaction temperature of about 100° C. may be employed. Generally, higher reaction temperatures and higher amounts of acid tend to reduce the reaction time.

The reaction may be conducted at pressures of from about atmospheric pressure, or about 14 psia to about 2000 psia, preferably at pressures less than about 1000 psia.

The process according to the present invention may be used for isomerization of a single starting isomer. In other embodiments, one, some, or all isomers in a mixture of starting isomers may be isomerized in accordance with the present invention. During or after the completion of the isomerization, the resulting product contains a mixture of isomers. However, not all possible isomers may be present in the final product and the amounts of isomers in the final product varies depending on the reaction conditions. For example, the present invention provides a unique method for isomerizing a mixture of disubstituted biaryl compounds, such as dialkylbiaryls so that the final product contains only 3,X', i.e. 3,3'-, 3,4'-isomers, and 4,4'-isomers and does not contain any of the 2,X'-isomers. The more linear 3,X'- and 4,4'-isomers, especially 3,4'and 4,4'-isomers are generally strongly preferred for further functionalization or as starting materials for production of high performance polymers, such as polyesters and polyamides.

In preferred embodiments of the invention a desired single isomer may be produced or its proportion in a mixture may be substantially increased. For example, production of 3,4'- or 4,4'-dimethylbiphenyl from another dimethylbiphenyl isomer or a mixture of dimethylbiphenyl isomers may be performed in accordance with the present invention. The starting isomer or a mixture of isomers is subjected to the isomerization reaction in the presence of a strong acid according to the isomerization method or process of the present invention. The starting isomer or a mixture of isomers of a substituted diaryl compound is isomerized until the reaction is complete to produce a first equilibrium or first near equilibrium mixture of isomers comprising a desired isomer.

In embodiments of the invention, the desired isomer (such as 3,4'- or 4,4'-dimethylbiphenyl) can then be selectively removed from the equilibrium mixture. Then, the remaining mixture can be re-isomerized or re-equilibrated by re-contacting it with the strong acid under isomerization conditions again to produce a second equilibrium or second near equilibrium mixture containing an equilibrium or near equilibrium amount of the desired isomer. The steps of re-isomerizing or re-equilibrating the remaining mixture may be repeated several times, wherein each time the desired isomer is removed prior to re-isomerizing or re-equilibration. The isomer that is removed after each re-isomerization step may be the same as or different from the desired isomer removed after the first or any other previous isomerization step (though removal of the same isomer with each step is generally preferred). The removed desired isomer isolated after each of the removal steps may be combined with the isomers removed after any other isolation and removal steps, or can be combined with a mixture of isomers recovered at the end of the process.

In other embodiments, the reaction at any one or more steps may be stopped prior to reaching equilibrium when the amount of the desired isomer reaches an acceptable or predetermined level.

The reactions of re-equilibration or re-isomerization may be conducted under the same conditions as the isomerization process described above, i.e. the temperatures, acids, acid/substrate ratios, times, and possible solvents suitable for the isomerization reaction of a single monomer or a mixture of isomers as disclosed above may be employed in the re-isomerization reactions.

The present invention is further illustrated in the following examples wherein all parts, percentages and ratios are by moles, all temperatures are in ° C. and all pressures are atmospheric or in psia unless otherwise indicated:

EXAMPLE 1

In this example, a single isomer, 4,4'-dimethylbiphenyl (dmbp), is isomerized in accordance with the isomerization process of the present invention. 4,4'-dimethylbiphenyl (dmbp) and triflic acid were charged in a Pyrex glass reactor equipped with a stirrer at an acid to dmbp ratio of 10 mol/mol. No solvent was used in the reaction. The reaction was allowed to continue for 67 hours at 25° C. Samples were withdrawn at 2, 18, 43 and 67 hours and were analyzed by GS/MS. The organic product was washed with water. The organic phase was separated and treated with sodium bicarbonate to remove the residual triflic acid in the organic layer. The results of GS/MS analysis are shown in Table 1.

EXAMPLES 2–3

In these examples, a single isomer, 4,4'-dimethylbiphenyl (dmbp), is isomerized in accordance with the isomerization process of the present invention. The procedure of Example 1 was followed except that different molar ratios (20:1 and 50:1) of triflic acid to dmbp was used. The results are shown in Table 1:

TABLE 1

Effect of Acid/Substrate Ratio on the Isomerization of 4,4'-Dimethylbiphenyl (dmbp) at Room Temperature

| | EXAMPLE 1 Triflic acid/Substrate = 10 | | | EXAMPLE 2 Triflic acid/Substrate = 20 | | | EXAMPLE 3 Triflic acid/Substrate = 50 | | |
|---|---|---|---|---|---|---|---|---|---|
| time, h | % 4,4'-dmbp | % 3,3'-dmbp | % 3,4'-dmbp | % 4,4'-dmbp | % 3,3'-dmbp | % 3,4'-dmbp | % 4,4'-dmbp | % 3,3'-dmbp | % 3,4'-dmbp |
| 0 | 100 | 0 | 0 | 100 | 0 | 0 | 100 | 0 | 0 |
| 2 | 71.5 | 2 | 26.5 | 8 | 7 | 85 | 3.5 | 7.5 | 89 |
| 18 | 28 | 18 | 54 | 4 | 29 | 68 | 1 | 27 | 73 |
| 43 | 7 | 30 | 62 | 14 | 28 | 58 | 3 | 30 | 67 |
| 67 | 7 | 36 | 56 | 7 | 33 | 60 | — | — | — |

Reaction temperature = 25° C.

EXAMPLE 4

In this example, a single isomer, 3,3'-dimethylbiphenyl (dmbp), is isomerized in accordance with the isomerization process of the present invention. The procedure of Example 1 was followed except that 3,3'-dmbp isomer was used instead of 4,4'-dmbp, and the reaction temperature was increased to 100° C. The reaction was allowed to run for 2 hours. Samples were withdrawn at 10 minutes, 30 minutes, 1 hour and 2 hours. The results are shown in Table 2.

EXAMPLE 5

In this example, a single isomer, 3,3'-dimethylbiphenyl (dmbp), is isomerized in accordance with the isomerization process of the present invention. The procedure of Example 4 was followed except that a different molar ratio, 25 mol/mol of triflic acid to 3,3'-dmbp was used. The results are shown in Table 2:

TABLE 2

Effect of Acid/Substrate Ratio On Isomerization of 3,3'-Dimethylbiphenyl at 100EC.

| | EXAMPLE 4 Triflic acid/Substrate = 10 | | | EXAMPLE 5 Triflic acid/Substrate = 25 | | |
|---|---|---|---|---|---|---|
| time, h | % 4,4' dmbp | % 3,3'-dmbp | % 3,4'-dmbp | % 4,4'-dmbp | % 3,3'-dmbp | % 3,4'-dmbp |
| 0.166667 | 8 | 39 | 49 | 5 | 38 | 55 |
| 0.5 | 8 | 39 | 49 | 6 | 37 | 55 |
| 1 | 8 | 39 | 49 | 6 | 37 | 55 |
| 2 | 9 | 39 | 49 | 5 | 38 | 55 |

EXAMPLES 6–7

In these examples, a single isomer, 3,3'-dimethylbiphenyl (dmbp), is isomerized in accordance with the isomerization process of the present invention. The procedure of Example 4 was followed except that the reaction was conducted at different temperatures, 30° C. and 50° C., and allowed to run for 94 hours. The results are shown in Table 3.

EXAMPLE 8

In this example, a single isomer, 3,3'-dimethylbiphenyl (dmbp), is isomerized in accordance with the isomerization process of the present invention. The procedure of Example 4 was followed except that the reaction was allowed to run for 94 hours. The results are shown in Table 3:

TABLE 3

Effect of Temperature on the Isomerization of 3,3'-Dimethylbiphenyl at an acid/Substrate Ratio of 10. (HOTf/substrate = 10)

| | EXAMPLE 6 Temperature = 30EC | | | EXAMPLE 7 Temperature = 50EC | | | EXAMPLE 8 Temperature = 100EC | | |
|---|---|---|---|---|---|---|---|---|---|
| time, h | % 4,4'-dmbp | % 3,3'-dmbp | % 3,4'-dmbp | % 4,4'-dmbp | % 3,3'-dmbp | % 3,4'-dmbp | % 4,4'-dmbp | % 3,3'-dmbp | % 3,4'-dmbp |
| 0.166667 | 0.5 | 95.5 | 4 | 3 | 68 | 29 | 8 | 39 | 49 |
| 0.5 | 1 | 90 | 9 | 8 | 44 | 48 | 8 | 39 | 49 |
| 1 | 2 | 84 | 14 | 8.5 | 42.5 | 49 | 8 | 39 | 49 |
| 2 | 3 | 76 | 21 | 9 | 39 | 52 | 9 | 39 | 49 |
| 24 | 5 | 52 | 43 | 9 | 39 | 52 | 9 | 39 | 49 |
| 94 | 8 | 31 | 51 | 9 | 39 | 52 | 9 | 39 | 49 |

EXAMPLES 9–11

In these examples, a single isomer, 4,4'-dimethylbiphenyl (dmbp), is isomerized in accordance with the isomerization process of the present invention. The procedure of Example 1 was followed except that the reaction temperatures were changed to 30° C. and 50° C. The results are shown in Table 4:

TABLE 4

Effect of Temperature on the Isomerization of 4,4'-Dimethylbiphenyl at an acid/Substrate Ratio of 10. (HOTf/substrate = 10)

| | EXAMPLE 9 Temperature = 25° C. | | | EXAMPLE 10 Temperature = 30° C. | | | EXAMPLE 11 Temperature = 50° 0.C | | |
|---|---|---|---|---|---|---|---|---|---|
| time, h | % 4,4'-dmbp | % 3,3'-dmbp | % 3,4'-dmbp | % 4,4'-dmbp | % 3,3'-dmbp | % 3,4'-dmbp | % 4,4'-dmbp | % 3,3'-dmbp | % 3,4'-dmbp |
| 2 | 71.5 | 2 | 26.5 | 11 | 12 | 77 | 7 | 36 | 57 |
| 18 | 28 | 18 | 54 | 7 | 30 | 63 | 6 | 37 | 57 |
| 43 | 7 | 30 | 62 | 7 | 35 | 58 | 7 | 37 | 56 |
| 67 | 7 | 36 | 56 | 7 | 37 | 55 | 8 | 37 | 52 |

EXAMPLES 12–16 and COMPARATIVE EXAMPLES 1–6

In these examples and comparative examples, a single isomer, 3,3'-dimethylbiphenyl (dmbp), is isomerized without a solvent and with various solvents. The 3,3'-dimethylbiphenyl (dmbp) and triflic acid were charged in a Pyrex glass reactor equipped with a stirrer at an acid to dmbp ratio of 10 mol/mol. No solvent was used in the Example 12 reaction. Various solvents were used in the reactions of Examples 13–16 and Comparative Examples 1–6. The acid/solvent molar ratio was 1 mole/mole and the substrate/solvent ratio was 0.05 mole/mole. Each reaction was allowed to continue for 94 hours at 25° C. Samples were withdrawn at 20 and 94 hours and were analyzed by GS/MS. The organic product was washed with water. The organic phase was separated and treated with sodium bicarbonate to remove the residual triflic acid in the organic layer. The results of GS/MS analysis are shown in Table 5. As evident from the results shown in Table 5, solvents which are aromatic compounds that have more than one alkyl substituent in the ring, such as xylenes, cumenes or 1,3,5 trimethylbenzene tend to inhibit the isomerization reaction:

TABLE 5

Effect of the Solvent on the Isomerization of 3,3'-Dimethylbiphenyl at Room Temperature Acid/Solvent ratio = 1 mole/mole
Reaction Temperature = 25° C.
Substrate/Solvent ratio = 0.05 mole/mole TABLE 5-continued Effect of the Solvent on the Isomerization of 3,3'-Dimethylbiphenyl at Room Temperature

| | | Reaction time | | | | | |
|---|---|---|---|---|---|---|---|
| | | 20 hours Composition | | | 94 hours Composition | | |
| Example | Solvent | % 4,4'-dmbp | % 3,3'-dmbp | % 3,4'-dmbp | % 4,4'-dmbp | % 3,3'-dmbp | % 3,4'-dmbp |
| 12 | none | 4 | 53 | 43 | 6 | 35 | 58 |
| 13 | benzene | 14 | 48 | 38 | 9 | 38 | 50 |
| 14 | toluene | 12 | 52 | 34 | 8 | 41 | 49 |
| 15 | n-octane | 6 | 58 | 34 | 9 | 41 | 47 |
| 16 | perfluorobenzene | 5 | 60 | 34 | 10 | 41 | 47 |
| Comparative Example 1 | p-xylene | 3 | 71 | 24 | 8 | 50 | 40 |
| Comparative Example 2 | m-xylene | 1 | 88 | 9 | 6 | 62 | 30 |
| Comparative Example 3 | o-xylene | 2 | 77 | 18 | 4 | 66 | 28 |
| Comparative Example 4 | cumene | 0 | 97 | 2 | 2 | 77 | 18 |
| Comparative Example 5 | p-cumene | 0 | 99 | 1 | 0 | 94 | 4 |
| Comparative Example 6 | 1,3,5-trimethylbenzene | 0 | 100 | 0 | 1 | 97 | 2 |

EXAMPLE 17

In this example, a mixture of isomers is isomerized in accordance with the isomerization process of the present invention. A mixture of 6 dmbp isomers obtained by oxidative coupling of toluene according to procedures described, for example, in U.S. Pat. Nos. 3,895,055 and 4,294,976, was combined together with triflic acid isomerization catalyst in a Pyrex glass reactor equipped with a stirrer at an acid to dmbp ratio of 3.6 mol/mol in the presence of toluene as a solvent. The dmbp to toluene ratio was about 5%. The molar ratio of triflic acid to toluene was about 0.18:1 The reaction was allowed to continue for 140 hours at 25° C. Samples were withdrawn at 20 and 140 hours and were analyzed by GS/MS. The results are shown in Table 6.

EXAMPLES 18–20

In these examples, a mixture of isomers, is isomerized in accordance with the isomerization process of the present invention. The procedure of Example 17 was followed except that the acid/dmbp ratio was changed to 18.1, 91.7 and 183.4 mol/mol. The molar ratio of triflic acid to toluene was about 0.90:1, 4.6:1, and 9.2:1, respectively. The results are shown in Table 6:

EXAMPLES 21–22

In these examples, a mixture of dimethyl biphenyl isomers is isomerized in accordance with the isomerization process of the present invention. The procedure of Example 17 was followed except that the reaction temperature was changed to 100° C. and the acid/substrate ratio was 5 and 10 mol/mol. The reaction was completed in 10 minutes. The results are shown in Table 7:

TABLE 7

Effect of Acid/substrate Ratio on the Isomerization at 100° C.
Of the Product of Toluene Coupling

| Isomers In Mixture | Substrate Composition Before Reaction | EXAMPLE 21 Acid/Substrate 5 | EXAMPLE 22 Acid/Substrate 10 |
|---|---|---|---|
| 2,2'-dmbp | 5% | 0.0 | 0.0 |
| 2,3'-dmbp | 18% | 1.6 | 0.5 |
| 2,4'-dmbp | 14% | 1.0 | 0.5 |
| 3,3'-dmbp | 24% | 39.3 | 39.3 |
| 3,4'-dmbp | 29% | 46.8 | 51.5 |
| 4,4'-dmbp | 10% | 11.3 | 8.2 |

Reaction time = 10 min
Isomerization is conducted in toluene at dmbp/toluene ratio = 5%

TABLE 6

Effect of Acid/substrate Ratio on the Isomerization at 20° C. of the Product of Toluene Coupling.

| | | Reactant Mixture | | | | | | | |
|---|---|---|---|---|---|---|---|---|---|
| | | EXAMPLE 17 | | EXAMPLE 18 | | EXAMPLE 19 | | EXAMPLE 20 | |
| Molar Ratio Triflic acid: Toluene | | 0.18 | 0.18 | 0.90 | 0.90 | 4.6 | 4.6 | 9.2 | 9.2 |
| Acid/Substrate | | 3.6 | 3.6 | 18.1 | 18.1 | 91.7 | 91.7 | 183.4 | 183.4 |
| Reaction time, h | 0 | 20 | 140 | 20 | 140 | 20 | 140 | 20 | 140 |
| 2,2'-dmbp % | 5 | 4.3 | 3.9 | 0.0 | 0.0 | 0.0 | 0.0 | 0.0 | 0.0 |
| 2,3'-dmbp % | 18 | 19.5 | 20.0 | 2.5 | 4.3 | 0.0 | 0.0 | 0.0 | 0.0 |
| 2,4'-dmbp % | 14 | 13.5 | 12.4 | 0.3 | 0.2 | 0.0 | 0.0 | 0.0 | 0.0 |
| 3,3'-dmbp % | 24 | 24.5 | 24.8 | 38.2 | 38.4 | 30.4 | 27.5 | 30.2 | 26.3 |
| 3,4'-dmbp % | 29 | 27.7 | 28.5 | 52.5 | 49.3 | 70.0 | 72.5 | 69.8 | 73.7 |
| 4,4'-dmbp % | 10 | 10.5 | 10.5 | 6.5 | 7.7 | 0.0 | 0.0 | 0.0 | 0.0 |

Isomerization is conducted in toluene at dmbp/toluene ratio = 5%

COMPARATIVE EXAMPLES 7–8

The procedure of Example 5 was followed in Comparative Examples 7 and 8 except that the triflic acid of Example 5 was substituted with trifluoroacetic acid (Hammett acidity −8), and 98% sulfuric acid (Hammett acidity −12.6), in Comparative Examples 7 and 8, respectively. The reaction time was 16 hours for trifluoroacetic acid in Comparative Example 7, and 42 hours for sulfuric acid in Comparative Example 8. No isomerization was observed when either trifluoroacetic acid or sulfuric acid were used.

As can be seen from the illustrative and comparative examples isomerization of substituted diaryl compounds can be achieved by treating a single isomer or a mixture of isomers with a strong acid. The reaction conditions such as temperature, acid/substrate ratio, and type and the amount of solvent can be varied to obtain resulting isomer mixtures containing different amounts of different isomers, thus allowing selective production of desired isomers in greater amounts. The choice of the acid catalyzing the isomerization and a solvent is very important for the isomerization process. Only very strong acids catalyze the isomerization and some solvents may inhibit the isomerization reaction.

What is claimed is:

1. A method for isomerizing at least one substituted diaryl compound comprising admixing at least one substituted diaryl compound with at least one strong acid to isomerize at least one substituted diaryl compound, wherein said at least one strong acid has a Hammett acidity of less than about −12.6.

2. A method as claimed in claim 1 wherein a mixture of substituted diaryl compounds is admixed with said strong acid.

3. A method as claimed in claim 1 wherein a single substituted diaryl compound is admixed with said strong acid.

4. A method as claimed in claim 1 wherein said at least one substituted diaryl compound includes at least one isomer which is substituted in at least the 2-position and said isomerization substantially reduces the amount of at least one isomer substituted in the 2-position.

5. A method as claimed in claim 1 wherein said isomerization substantially increases the amount of at least one isomer substituted in at least the 3-position.

6. A method as claimed in claim 1 wherein said isomerization substantially increases the amount of at least one isomer substituted in at least the 4-position.

7. A method as claimed in claim 1 wherein said isomerization substantially increases the amount of at least one isomer substituted in at least the 3-position and the 4'-position.

8. A method as claimed in claim 4 wherein said isomerization substantially increases the amount of at least one isomer substituted in at least the 3-position and the 4'-position.

9. A method as claimed in claim 1 wherein said at least one substituted diaryl compound is at least one substituted diaryl compound represented by the formula (A)

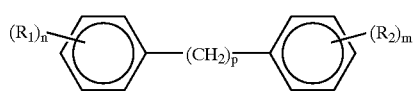

(A)

wherein n and m may be the same or different and are integers from 1 to 4, p is an integer from 0 to 10, each $R_1$ can be the same or different, each $R_2$ can be the same or different, and $R_1$ and $R_2$ may be the same or different and are selected from electron donating substituent groups.

10. A method as claimed in claim 9, wherein $R_1$ and $R_2$ are selected from alkyl, aryl, alkoxyl or hydroxyl groups.

11. A method as claimed in claim 1, wherein the molar ratio of said at least one acid to said at least one substituted diaryl compound is from about 1:1 to about 200:1.

12. A method as claimed in claim 1, wherein said strong acid is triflic acid.

13. A method as claimed in claim 1, wherein said at least one acid is a mixture of triflic acid and trifluoroacetic acid.

14. A method as claimed in claim 1, wherein said isomerization reaction is conducted at a temperature of from about −10° C. to about 300° C.

15. A method as claimed in claim 1, wherein said isomerization reaction is conducted at a temperature of from about 20° C. to about 150° C.

16. A method as claimed in claim 1, wherein said isomerization reaction is conducted for time from about 2 minutes to about 100 hours.

17. A method as claimed in claim 1, wherein said isomerization reaction is conducted in the absence of a catalyst other than said at least one strong acid.

18. A method as claimed in claim 1, wherein said isomerization reaction is conducted in the absence of a solvent other than said strong acid.

19. A method as claimed in claim 1, comprising a step of admixing said at least one substituted diaryl compound with a solvent.

20. A method as claimed in claim 19, wherein said solvent is selected from unsubstituted or monosubstituted alkyl aromatic solvents, halogenated aromatic solvents, paraffinic solvents represented by the formula $C_nH_{2n+2}$, wherein n is an integer from 8 to about 30, and mixtures thereof.

21. A method as claimed in claim 20, wherein said solvent is selected from benzene, toluene, perfluorobenzene, and n-octane.

22. A method as claimed in claim 21, wherein the weight ratio of said at least one diaryl compound to said solvent is from about 0.01:1 to about 1:1.

23. A method as claimed in claim 9, wherein n=m=1.

24. A method as claimed in claim 23, wherein p=0.

25. A method as claimed in claim 24, wherein $R_1$ and $R_2$ are selected from alkyl or aryl groups.

26. A method as claimed in claim 25, wherein said at least one substituted diaryl compound is dimethylbiphenyl.

27. A method as claimed in claim 19, wherein the molar ratio of said at least one strong acid to said solvent is from about 0.1 to about 15.

28. A method as claimed in claim 19, wherein the molar ratio of said strong acid to said solvent is from about 0.8:1 to about 10:1.

29. A method as claimed in claim 26, wherein the final product of said isomerization reaction does not contain any 2,X'-isomers where X' is an integer from 2 to 4.

30. A method as claimed in claim 1 further comprising a step of separating a single desired isomer from the reaction mixture subsequent to the isomerization reaction.

31. A method for producing a single isomer of a substituted diphenyl compound comprising:

a) subjecting at least one isomer of a substituted diphenyl compound to an isomerization reaction in the presence of at least one strong acid having a Hammett acidity of −12.6 or less to produce a first equilibrium mixture of isomers comprising a desired isomer, b) removing the desired isomer from said mixture of isomers, and c) re-isomerizing the remaining isomers to produce a second equilibrium mixture of isomers comprising said desired isomer.

32. A method as claimed in claim 31, wherein said substituted diphenyl compound is represented by the formula (A):

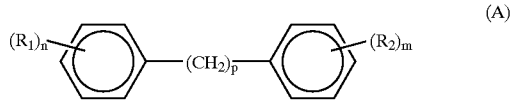

(A)

wherein n and m may be the same or different and are integers from 1 to 4, p is an integer from 0 to 10, each $R_1$ can be the same or different, each $R_2$ can be the same or different, and $R_1$ and $R_2$ may be the same or different and are selected from electron donating substituent groups.

33. A method as claimed in claim 32, wherein n=m=1 and p=0.

34. A method as claimed in claim 33, wherein said at least one strong acid is triflic acid.

35. A method as claimed in claim 33, wherein said isomerization reaction and said re-isomerizing are conducted at a temperature of from about −10° C. to about 300° C.

36. A method as claimed in claim 35, wherein said isomerization reaction and said re-isomerizing are conducted at a temperature of from about 20° C. to about 150° C.

37. A method as claimed in claim 33, wherein said isomerization reaction is conducted in the absence of a catalyst other than said at least one strong acid.

38. A method as claimed in claim 33, wherein said isomerization reaction is conducted in the absence of a solvent other than said at least one strong acid.

39. A method as claimed in claim 33, comprising a step of admixing said at least one isomer of a substituted diaryl compound with a solvent.

40. A method as claimed in claim 39, wherein said solvent is selected from benzene, toluene, perfluorobenzene, paraffinic solvents represented by the formula $C_nH_{2n+2}$, wherein n is an integer from 8 to about 30, and mixtures thereof.

41. A method as claimed in claim 33, wherein $R_1$ and $R_2$ are both methyl groups.

42. A method as claimed in claim 41, wherein said desired isomer is 4,4'-dimethylbiphenyl.

43. A method as claimed in claim 41, wherein said desired isomer is 3,4'-dimethylbiphenyl.

44. A method as claimed in claim 31 further comprising recovering the second equilibrium mixture of isomers from the reaction media.

45. A method as claimed in claim 44, wherein said removed desired isomer is combined with said recovered second equilibrium mixture of isomers.

46. A method as claimed in claim 31 further comprising d) removing a second desired isomer from the said second mixture of isomers.

47. A method as claimed in claim 46 wherein the desired isomer removed in step d) is the same isomer as the desired isomer removed in step b).

48. A method as claimed in claim 46 further comprising combining the desired isomer removed in step b) with the desired isomer removed in step d).

49. A method as claimed in claim 46, further comprising repeating steps c) and d) up to 5 times.

* * * * *